(12) United States Patent
Caulfield

(10) Patent No.: US 6,545,945 B2
(45) Date of Patent: Apr. 8, 2003

(54) MATERIAL CLASSIFICATION APPARATUS AND METHOD

(75) Inventor: David D. Caulfield, Stony Plain (CA)

(73) Assignee: Ocean Data Equipment Corporation, Providence, RI (US)

( * ) Notice: Subject to any disclaimer, the term of this patent is extended or adjusted under 35 U.S.C. 154(b) by 54 days.

(21) Appl. No.: 09/791,671

(22) Filed: Feb. 26, 2001

(65) Prior Publication Data

US 2002/0159334 A1 Oct. 31, 2002

(51) Int. Cl.[7] .............................................. G01S 15/00
(52) U.S. Cl. ............................. 367/87; 367/135; 342/22
(58) Field of Search ......................... 367/87, 124, 135; 342/22, 189, 195

(56) References Cited

U.S. PATENT DOCUMENTS

| | | | |
|---|---|---|---|
| 4,855,911 A | 8/1989 | Lele et al. | 73/602 |
| 4,922,467 A | 5/1990 | Caulfield | 367/87 |
| 5,563,848 A | 10/1996 | Rogers et al. | 367/99 |
| 5,974,881 A | 11/1999 | Donskoy et al. | 367/87 |
| 5,979,240 A | 11/1999 | Rix et al. | 73/602 |
| 6,044,336 A | 3/2000 | Marmarelis et al. | 367/87 |
| 6,366,232 B1 * | 4/2002 | Liedtke et al. | 342/22 |

* cited by examiner

Primary Examiner—Daniel T. Pihulic

(57) ABSTRACT

The present invention provides signification improvements over the apparatus and method disclosed by U.S. Pat. No. 4,922,467. The invention provides an apparatus for material classification and substance identification of an object contained within an enclosure, or buried beneath the ground. The improvements to the present invention include the use of a source of either electromagnetic or acoustic energy, and electromagnetic or acoustic energy receivers, as appropriate. In addition, the present invention discloses the use of energy pulses of differing frequencies, such that the signal processor can compute the rate of change of energy absorption of the substance, as a function of frequency ($d\alpha/df$). In this way, the apparatus permits the formulation of a highly detailed and accurate object signature, which can be compared with a database of known object signatures for exact substance identification.

26 Claims, 7 Drawing Sheets

MATERIAL CLASSIFICATION APPARATUS AND METHOD

The present invention relates to the field of substance identification from a remote location. More particularly, the invention provides significant improvements over previous U.S. Pat. No. 4,922,467, issued on May 1, 1990. The original patent disclosed an acoustic detection apparatus for characterization of an object within an enclosure, or buried beneath the ground. For this purpose, U.S. Pat. No. 4,922,467 disclosed an apparatus that transmits acoustic energy towards the object, and subsequently detects and analyzes the energy reflected and refracted/transmitted by the object. By comparing the transmitted, reflected, and refracted/transmitted energy, the apparatus can assign a signature to the object, and compare the signature with a database of signatures of known objects, thus identifying the object.

The apparatus of the present application provides significant improvements over the original patent, by allowing highly accurate characterization of a substance that is enclosed within a container. The improved material classification technique involves application of acoustic or electromagnetic (EM) energy to the container, and detection of both the reflected and refracted/transmitted energy therefrom. Subsequent analysis of the time and energy content of the detected signals allows computation of acoustic/EM energy impedance, acoustic/EM energy absorption, and acoustic/EM wave velocity changes that are conferred on the reflected and transmitted/refracted signals by the presence of the substance. These values allow sound predictions to be made regarding the mechanical properties of the substance, thus providing the substance with a specific signature. Comparison of the signature with a database of known signatures permits identification of the substance. The present invention can also analyze the absorption characteristics of the substance over a range of frequencies. In this way, the apparatus allows computation of additional parameters involving absorption as a function of frequency. These additional parameters allow the formulation of a highly detailed signature for each substance. The improvements over U.S. Pat. No. 4,922,467 therefore permit the apparatus to identify a considerably wider range of substances with increased accuracy. For specific classes of substances, analysis of the absorption/frequency characteristics alone can be sufficient for accurate substance identification.

Analysis of reflected acoustic energy is well known in the art to facilitate identification of a substance concealed beneath an outer layer. For example, U.S. Pat. No. 5,979,240 issued Nov. 9, 1999, discloses a device for detecting recyclable plastic and metal items within solid waste. Acoustic energy of a fixed wavelength is transmitted into the waste causing specific substances to resonate. Detection of the resonating energy allows the recyclable items to be located. Other such devices are directed towards medical uses. For example U.S. Pat. No. 4,855,911 issued Aug. 8, 1989, provides a device for transmitting ultrasound into tissues and detecting the back-scatter energy reflected from buried anomalies within the tissue. Still further devices, such as those disclosed by U.S. Pat. No. 5,563,848 issued Oct. 8, 1996, and U.S. Pat. No. 5,974,881 issued Nov. 2, 1999, detect the presence of objects buried within the ground. Sound waves are transmitted into the ground, and the nature of the energy reflected by the buried object is detected and analyzed.

It is important to note that the devices disclosed by the cited references specifically involve detection of reflected acoustic energy. By limiting analysis to reflected energy, the parameters for substance determination are limited. For this reason, U.S. Pat. No. 4,922,467, which is incorporated herein by reference, provides a preliminary means for material classification by simultaneous analysis of both reflected and refracted/transmitted acoustic energy, thus providing each substance with a unique and characteristic signature. The present application further expands and refines the accuracy and flexibility of the apparatus disclosed by U.S. Pat. No. 4,922,467. The improved apparatus therefore provides both rapid and highly accurate substance determination.

SUMMARY OF THE INVENTION

In accordance with the present invention, "enclosure" is defined as being a hollow box-like structure containing an object to be detected and identified with respect to its constituents. The apparatus disclosed permits reliable, accurate and non-invasive identification of enclosed materials, and can have a number of important applications.

In a first embodiment, the present invention provides a means for detecting illegal substances such as drugs and explosives within suitcases and baggage, without the need for time-consuming human intervention. Current systems for analyzing the contents of a suitcase include X-ray scanning machines and animals trained for chemical sniffing. However, these systems are labor intensive. Moreover, visual scanning of X-ray images is prone to human error, since illegal substances may appear similar to those which are legal. Animals can be trained to detect the scent of specific chemicals, but the number and range of substances may be restricted, and such substances may be masked by other smells to prevent their detection. It is therefore desirable to develop more accurate, automated techniques for the detection of illegal substances within suitcases and other baggage. In particular, by using a wider frequency range of energy input (including EM radiation), and by analyzing energy absorption properties over a range of frequencies, the present invention permits highly accurate identification of substances within an enclosure. The devices of the present invention may be arranged as an array over a conveyor, thus mapping the contents of the suitcases as they are transported horizontally along the conveyor. In addition, the present apparatus does not require shielding from the operator or public, since harmless acoustic or electromagnetic energy may be used by the device. This contrasts with the X-ray devices presently used for luggage analysis, which require shielding and potentially dangerous radiation.

In a second embodiment, the invention may be used to detect the presence of substances buried beneath the surface of the earth. For example, the apparatus of the present invention can determine the location of pipelines or other enclosures containing oil, gas or chemicals. Importantly, once the enclosure or pipeline has been located, the present invention may be used to quickly and accurately characterize the nature of the substance contained within the enclosure or pipeline. In this regard, it is well known in the art that acoustic waves may be bounced off the ocean floor, in order to determine the nature of the material from which sediment layers are comprised. The present invention provides for significant additions and enhancements to these previous techniques, permitting the formulation of detailed signatures for different types of substances.

In a third embodiment, the invention may be used to detect the presence of explosives buried beneath the ground. For example, a potentially explosive land mine may be differentiated from spent shrapnel or other scrap metal by the detection of explosive substances enclosed within the body of the mine. The invention presents a significant advantage in that the mine may be detected and characterized whilst still underground, without the need for disturbing the mine and risking detonation.

The apparatus of the present invention comprises a transmitter device for directing a pulse of EM or acoustic energy towards the enclosure that contains the unknown substance. The energy may be in the form of a specific pulse, or may be random noise. The energy is reflected from any intercepted interface, which may include the surface of the enclosure, and the surface of the substance to be detected within. The duration and intensity of the reflected energy can be detected by a first receiver (EM or acoustic). A proportion of the EM or acoustic energy is also refracted and/or transmitted from the substance within the container, and the duration and intensity of this refracted/transmitted energy may be detected by a second receiver. When a pulse of initial energy is transmitted towards the object, specific features of the reflected and refracted pulses can be measured and compared with the original pulse. When random noise is used, more complex processing may be carried out by correlation techniques that are well known in the art. In this way, the incident, reflected, and transmitted/refracted random noise energy can be compared and differentiated from background noise.

A signal processor, connected to the transmitter and the first and second receivers, processes the information regarding the transmitted and received energy, thus producing an object signature indicative of the substance. A comparator is also provided to compare the object signature with those of known substances stored in a computer database. The computer determines a match, or a closest possible match, thus identifying the substance.

The optional use of EM transmitters and receivers in the apparatus of the present invention greatly enhances the scope of signature matrices that may be provided for a particular substance. Moreover, the present invention significantly improves the accuracy and range of material types that may be detected and characterized. This is attributable in part to the capacity of the apparatus to transmit and receive energy of varying frequencies. Thus over a range of frequencies the absorption characteristics of the substance may be determined. By analysis of the rate of change of absorption with respect to frequency, additional important information regarding the mechanical properties of the substance is provided, greatly enhancing the detail of the substance signature. Moreover, the detailed signature provides a more refined and accurate representation of the substance, permitting a much larger range of substances to be differentiated from one another.

In accordance with one aspect of the invention there is provided an apparatus for detecting the substance of an object contained within an enclosure, the apparatus comprising: electromagnetic or acoustic energy transmitter means for transmitting at least two pulses of electromagnetic or acoustic energy at a first side of the enclosure; first electromagnetic or acoustic energy receiver means for receiving electromagnetic or acoustic energy that has been reflected from the object to produce at least two reflected electromagnetic or acoustic energy signals; second electromagnetic or acoustic energy receiver means for receiving electromagnetic or acoustic energy that has been transmitted or refracted through the object to produce at least two transmitted or refracted electromagnetic or acoustic energy signals; signal processor means connected to said transmitter means and to said first and second receiver means for producing an object signature, wherein said object signature is generated by computing energy absorption for each frequency and calculating a rate of change of said energy absorption as a function of frequency; and comparator means for comparing said object signature with signatures of known objects to determine the substance of said object.

In accordance with another aspect of the invention there is provided an apparatus for detecting the substance of an object contained within an enclosure, the apparatus comprising: electromagnetic energy transmitter means for transmitting a pulse of electromagnetic energy at a first side of the enclosure; first electromagnetic energy receiver means for receiving electromagnetic energy that has been reflected from the object to produce a reflected electromagnetic energy signal; second electromagnetic energy receiver means for receiving electromagnetic energy that has been transmitted or refracted through the object to produce a transmitted or refracted electromagnetic energy signal; signal processor means connected to the transmitter means and to the first and second receiver means, the signal processor means processing the transmitted pulse of electromagnetic energy, the reflected electromagnetic energy signal, and the refracted or transmitted electromagnetic energy signal to produce an object signature indicative of the object; and comparator means for comparing the object signature with the signature of known objects to determine the substance of the object.

In accordance with still another aspect of the invention there is provided a method of determining the substance of an object located within an enclosure, the method comprising the steps of: applying at least two pulses of electromagnetic or acoustic energy each of known intensities and differing frequencies to a first side of the enclosure and the object in the enclosure; detecting at least two pulses of reflected electromagnetic or acoustic energy reflected from a surface of the object to provide reflected electromagnetic or acoustic energy signals; detecting at least two pulses of transmitted or refracted electromagnetic or acoustic energy transmitted or refracted through the object to provide transmitted or refracted electromagnetic or acoustic energy signals; processing the reflected and transmitted or refracted electromagnetic or acoustic energy signals to produce an object signature, the object signature comprising the electromagnetic or acoustic energy absorption of the substance as a function of frequency; and comparing the object signature so obtained with signatures of known objects to determine the substance of the object.

In accordance with yet another aspect of the invention there is provided a method of determining the substance of an object located within an enclosure, the method comprising the steps of: applying a pulse of electromagnetic energy of a known level to a first side of the enclosure and the object in the enclosure; detecting the reflected electromagnetic energy reflected from a surface of the object to provide a reflected electromagnetic energy signal; detecting the transmitted or refracted electromagnetic energy transmitted or refracted through the object to provide a transmitted or refracted electromagnetic energy signal; processing the reflected and transmitted or refracted electromagnetic energy signals to produce an object signature; and comparing the object signature so obtained with signatures of known objects to determine the substance of the object.

BRIEF DESCRIPTION OF THE DRAWINGS

The present invention will be discussed in detail with the aid of the accompanying drawings, in which.

DETAILED DESCRIPTION OF THE PREFERRED EMBODIMENTS

Figure 1A:
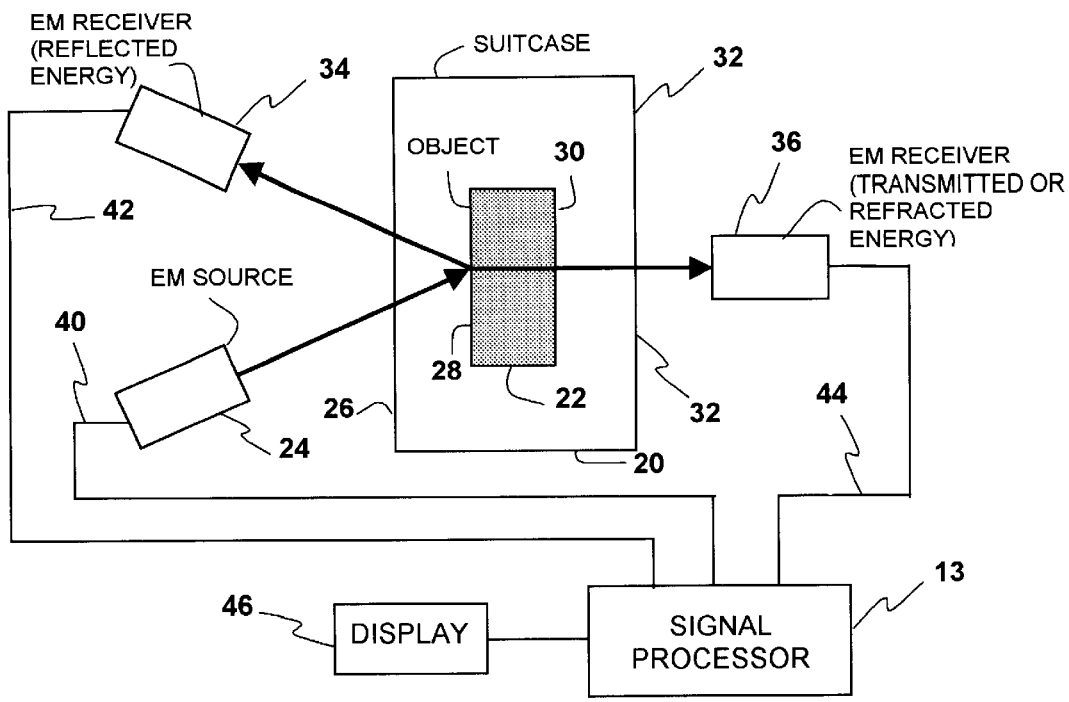
FIGS. 1a and 1b are schematic representations of the first and second embodiments of the present invention respectively, in which electromagnetic energy is used to characterize a substance within an enclosure.

With respect to FIG. 1a, a suitcase 20 contains an object 22, the substance of which is to be determined.

An electromagnetic energy transmitter 24 of known type is aimed at a side 26 of the suitcase 20. Signal processor 13 produces an electrical pulse which is sent by line 40 and is converted into an electromagnetic pulse by electromagnetic transmitter 24, which subsequently sends a pulse of electromagnetic energy of known intensity at side 26. Some of the energy of the pulse is reflected off the surface 26 and some of the energy of the pulse penetrates the suitcase and comes into contact with the object 22. Because the object 22 has different properties than the air in the suitcase, a portion of the energy of the pulse is reflected off the surface 28 of object 22. A further portion of the energy of the transmitted pulse is transmitted or refracted through object 22. Some of this remaining electromagnetic energy is reflected off the back surface 30 of the object as this surface also represents an interface between objects having differing electromagnetic impedancies. Some of the energy of the transmitted pulse penetrates the back side of the suitcase 32. The energy of the pulse that is reflected is received by a first electromagnetic receiver 34, located on the same side of the suitcase 20 as the electromagnetic transmitter 24. The energy of the pulse that has penetrated the suitcase and the object 22 exits the suitcase from side 32 and is detected by a second electromagnetic receiver 36. The electromagnetic receiver 36 could be placed at the longitudinal sides of the suitcase to detect the refracted energy. In this manner, multiple receivers could be employed as required by the application (see later).

Signal processor 13 generates and stores the electrical parameters such as pulse width and the energy of the electrical pulse fed to the electromagnetic transmitter 24. The received signals from electromagnetic receivers 34 and 36 are sent to signal processor 13 on lines 42 and 44, respectively.

Signal processor 13 processes the received signals with respect to the transmitted pulse and determines the electromagnetic impedance, the electromagnetic absorption, and the electromagnetic velocity of the transmitted signal in the object 22, to determine its electromagnetic signature. The parameters are further processed to determine the materials bulk density, bulk modulus, porosity, etc. When combined with the impedance, absoption and velocity, these values form the electromagnetic signature for the object. The signature is then compared to known electromagnetic signatures stored in processor 13, and the type of substance of object 22 is determined. This information is then outputted on display 46, which may be a monitor screen or a printer.

Figure 1B:
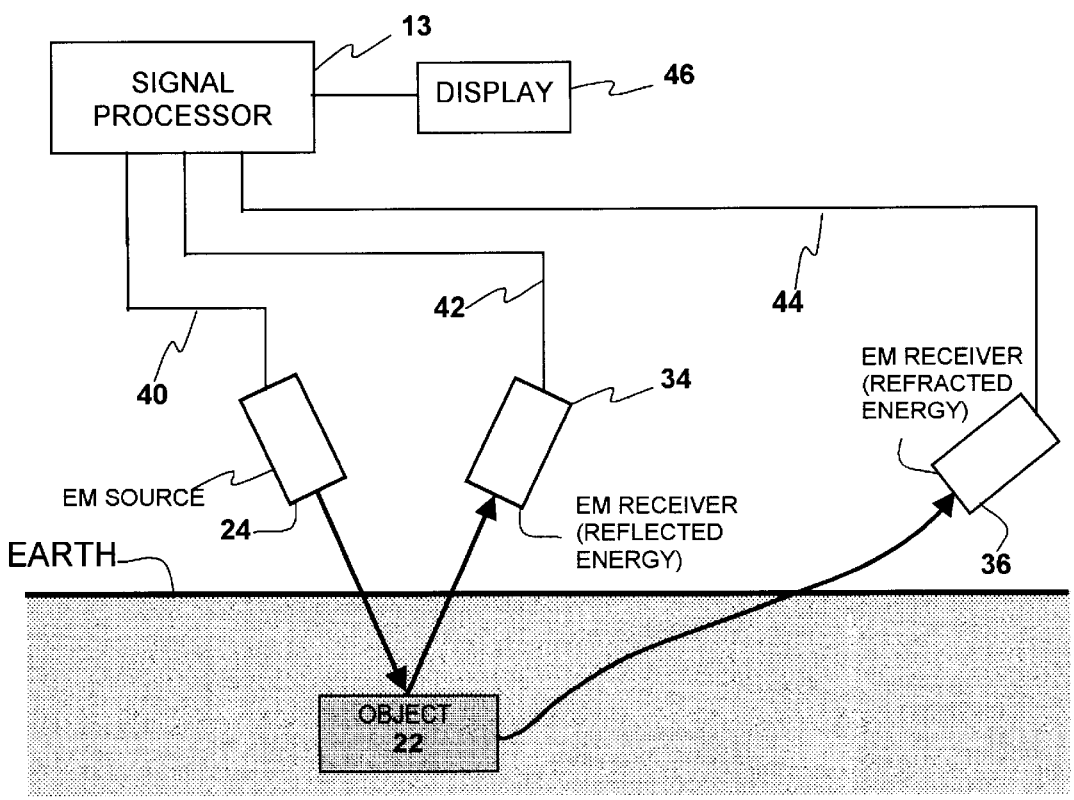

FIG. 1b shows an embodiment of the invention that detects and determines the substance of an object buried beneath the earth. Signal processor 13 produces an electrical pulse which is sent by line 40 and is converted into an electromagnetic pulse by electromagnetic transmitter 24. The electromagnetic pulse is aimed at the earth and moved about until the display 46 indicates the presence of an object. This occurs when the electromagnetic pulse penetrates the earth and hits object 22. A portion of the electromagnetic pulse is reflected from the surface of the object and the reflected energy is received by a first electromagnetic receiver 34. A portion of the transmitted pulse is refracted by object 22, and is directed out of the side of the object in a direction generally perpendicular to the direction of the transmitted pulse. A portion of the refracted electromagnetic energy is received by a second electromagnetic receiver 36. It must be noted that the two receivers 34 and 36 are both located above the earth. In order that receiver 36 detect the refracted energy, it must be positioned at a greater horizontal distance from the object that the receiver 34. Receivers 34 and 36 are connected to the signal processor 13 by lines 42 and 44, respectively. The remainder of the operation of this embodiment is the same as described with respect to FIG. 1a.

Figure 2:
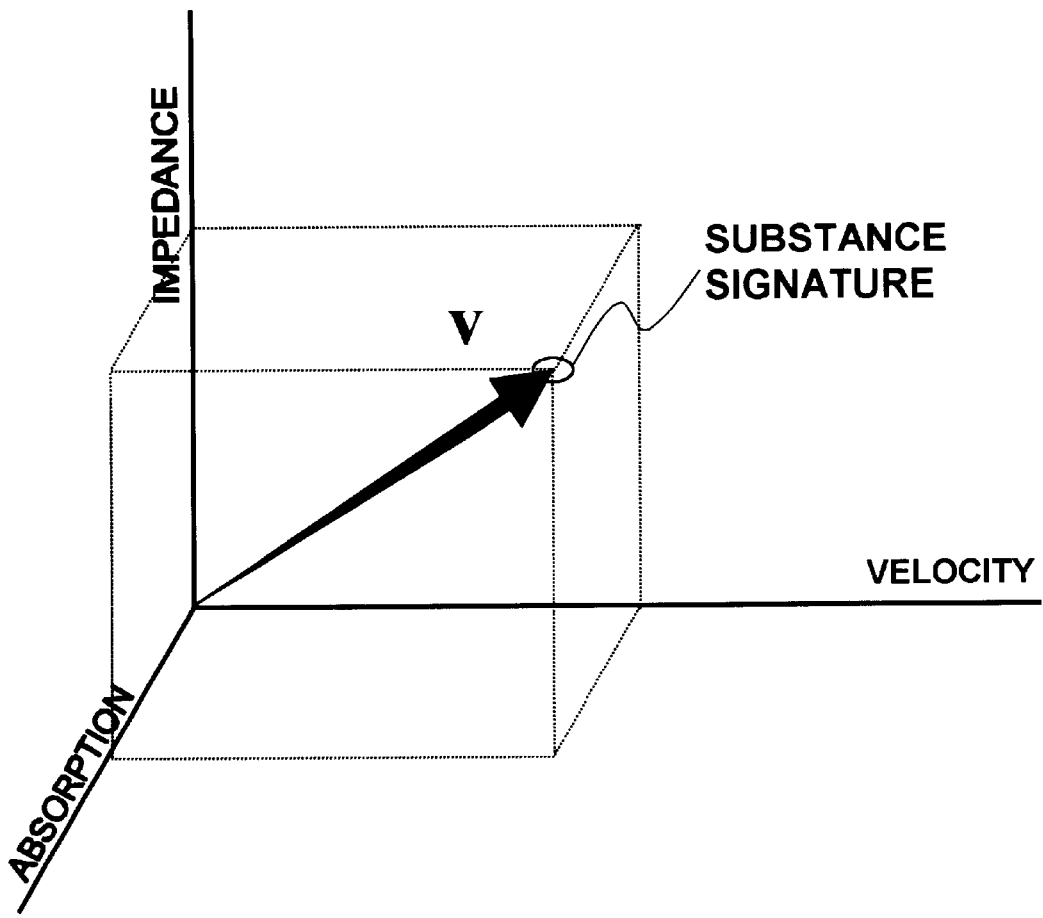
FIG. 2 Schematic representation of the material signature by a vector corresponding to three factors: impedance, velocity, and absorption.

The preliminary electromagnetic object signature of the unknown substance, as computed by the signal processor, is comprised of three factors, namely impedance, velocity and absorption. U.S. Pat. No. 4,922,467 provides for calculation of these three factors by analyzing the influence of the substance on acoustic energy. However, by considering these three factors alone, the system is limited in accuracy and flexibility. The three factors of impedance, velocity and absorption are represented schematically in FIG. 2. Each factor may be considered as an axis of the 3-dimensional graph shown in FIG. 2, the x-axis representing velocity, the y-axis representing impedance, and the z-axis representing absorption. By this representation, the vector 'v' indicates a position within the space of the graph that is indicative of the object signature of the substance. Each substance has differing values of velocity, impedance and absorption. In this way, each substance will be represented by an alternative vector and object signature. However, it is important to note that this system may not permit adequate differentiation of substances from one another. In particular, different substances within specific classes may exhibit vectors that are similar, if not indistinguishable from one another. This possibility complicates analysis of output data from the system, since a specific vector may, for example, indicate both a legal or an illegal substance. Moreover, these complications are exacerbated by signal noise generated by reflected and refracted/transmitted energy that originates from materials other than the unknown substance. In this regard, the present invention provides significant improvements to U.S. Pat. No. 4,922,467, thus permitting accurate differentiation of similar substances, as well as analysis of a wide range of substance types.

One improvement to U.S. Pat. No. 4,922,467 involves the addition of a fourth dimension to the graph shown in FIG. 2. Specifically, the present application discloses that for many materials, the absorption of either acoustic or electromagnetic energy is a linear function of frequency (over a specific frequency range). The relationship between absorption and frequency permits calculation of the rate of change of absorption with respect to frequency. Moreover, the energy transmitted through or reflected from any medium is a function of the reflection coefficient (R) and the absorption ($\alpha$) in decibels per meter (db/m), when corrected for boundary conditions and transmission loss effects. This leads to a generalized equation (1) for the received energy (S), as shown below.

$$S = \text{function } (A, R, \alpha) \quad (1)$$

Where
- A=The source energy or incident energy amplitude.
- R=The reflection coefficient, which is proportional to the impedance of the associated materials.
- $\alpha$=The absorption of the material or target (object) or layer(s) under analysis.

In equation (1), the received energy can be converted to spectral information by the use of Fourier Transforms, wavelets analysis or filtering. Alternatively, pulses of varied frequencies may be applied to the object. The differentiation of the data with respect to frequency (f) is provided in equation (2). In equation (2) the reflection coefficient (R) has been removed, since this term is not a function of frequency.

$$ds/df = \text{function } (dA/df, d\alpha/df) \quad (2)$$

In equation (2), the source or incident energy (A) is generally known, and therefore the function of the absorption with respect to frequency can be readily determined. Importantly, in a system where the incident energy (A) remains constant regardless of frequency, the value of ($d\alpha/df$) may be calculated without knowing the intensity of the source or incident energy. In this case, ($ds/df$) will be directly proportional to ($d\alpha/df$).

Experimental testing has shown that impedance and velocity are generally not a function of frequency, and are therefore unsuitable parameters for analysis with respect to frequency. Since absorption is a function of frequency (over a certain frequency range), calculations of ($d\alpha/df$) may be readily included in the test object signature.

The absorption calculations must allow for any geometrical layer scattering and/or non-plane wave propagation of the incident energy. These complications can arise when, for example, the surface of an object within a suitcase does not have a uniform consistency, or has an irregular shape. Similar complications arise when analyzing objects beneath the ground when the surface of the ground is uneven. Poorly defined interfaces can result in energy being reflected and refracted in additional directions to those indicated in FIGS. 1a and 1b. Although these issues complicate analysis of the object substance signature, means can be introduced to differentiate the principle energy deflections from those arising from background noise and interface conditions. The raw data generated by the receiver(s) can be refined by computer-aided correlation techniques, which filter the substance signature information from two types of noise. Firstly, the signal to noise ratio is improved by the enhancement of the signal information over the background noise.

Secondly, the principle signal generated by the object (according to FIGS. 1a and 1b) can be differentiated from unwanted noise resulting from layer scattering and non-plane wave propagation. Digital filters may be designed for optimal clean-up of both types of noise, according to the prevailing conditions. For example, measurements of ocean floor sediments may require filtering techniques that differ considerably from those of suitcase analysis.

Figure 3A:
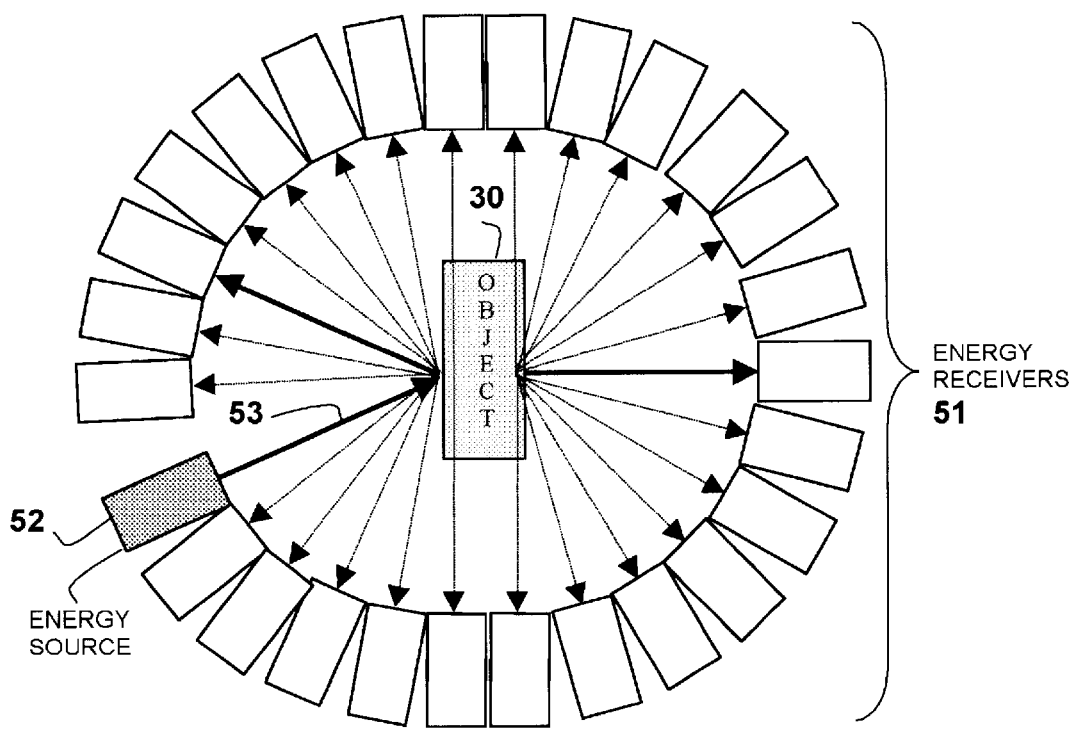
FIGS. 3a and 3b are schematic representations of preferred embodiments of the apparatus of the present invention, wherein multiple receivers (FIG. 3a) or a movable scanning receiver (FIG. 3b) may be used to receive energy emitted at additional angles relative to the incident energy.
Figure 3B:
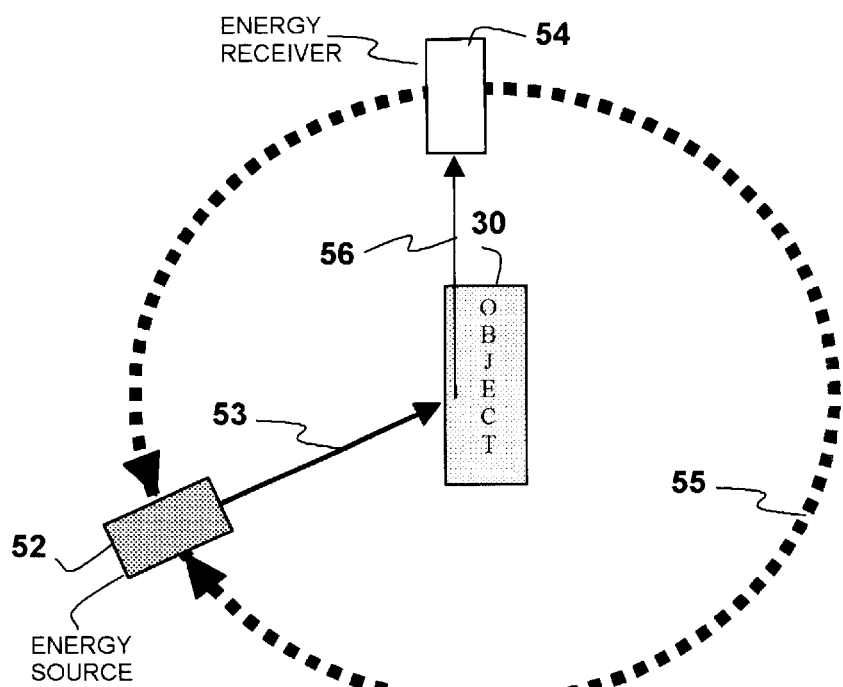

Further means to differentiate the principle energy deflections can involve the use of multiple receivers, or the arrangement of a movable 'scanning' receiver, which allows the generation of an overall 'picture' of the energy being reflected or refracted from the object under analysis. In this regard, a preferred embodiment of the present invention is shown in FIG. 3a, which provides for multiple receivers 51 arranged around the object 30 under analysis. A beam of energy 53 (electromagnetic or acoustic) is transmitted from an energy source 52 towards the object 30. The reflected, transmitted and refracted energy emitted from the object is detected by the array of receivers 51, each at differing angles relative to the incident energy. The signals generated by the multiple receivers are sent to the signal processor, and processed to compute an overall 'picture' of the energy emanating from the object. Correlation and filtering techniques allow improvements in signal-to-noise ratio, permitting differentiation of the principle reflected and transmitted/refracted energy signals, from those originating from background noise, layer scattering and non-plane wave propagation. The use of multiple receivers therefore increases the possibility of detecting the principle reflected and transmitted/refracted energy at optimal positions around the object. In an alternative embodiment (see FIG. 3b), a single receiver 54 can move around the object 30 along track 55. In this way, the receiver can be positioned at various angles relative to the incident energy 53, and the energy 56 emitted from the object can be analyzed at each position. The signals received at each position are sent to the signal processor, which processes the information as described for FIG. 3a.

In some cases it will not be possible to position receivers at all locations around the object (e.g. where the object is buried beneath the ground). Nonetheless, the use of multiple receivers or a moveable scanning receiver may still permit a significant amount of data to be gathered.

For accurate determination of substance signature, a narrow, focussed incident energy beam width may typically be used. However, sources of focussed (acoustic or EM) beams are generally more expensive than wider, less-focussed beam sources. For this reason it is desirable to use sources that generate wider energy beams to reduce the cost of the apparatus. Unfortunately, wider beams present significant disadvantages regarding signal to noise ratios. Specifically, noise resulting from layer scattering and non-plane wave propagation is increased due to the incident energy being spread across a larger area of uneven or non-uniform surface, thus increasing the quantity of irregularly reflected and refracted energy. Digital filters may be incorporated into the apparatus of the present invention, to significantly improve the signal to noise ratio of energy received from wide beam width incident energy. In this way, the cost of the apparatus may be considerably reduced by using less focussed sources of incident energy.

EXAMPLE 1

Figure 4:
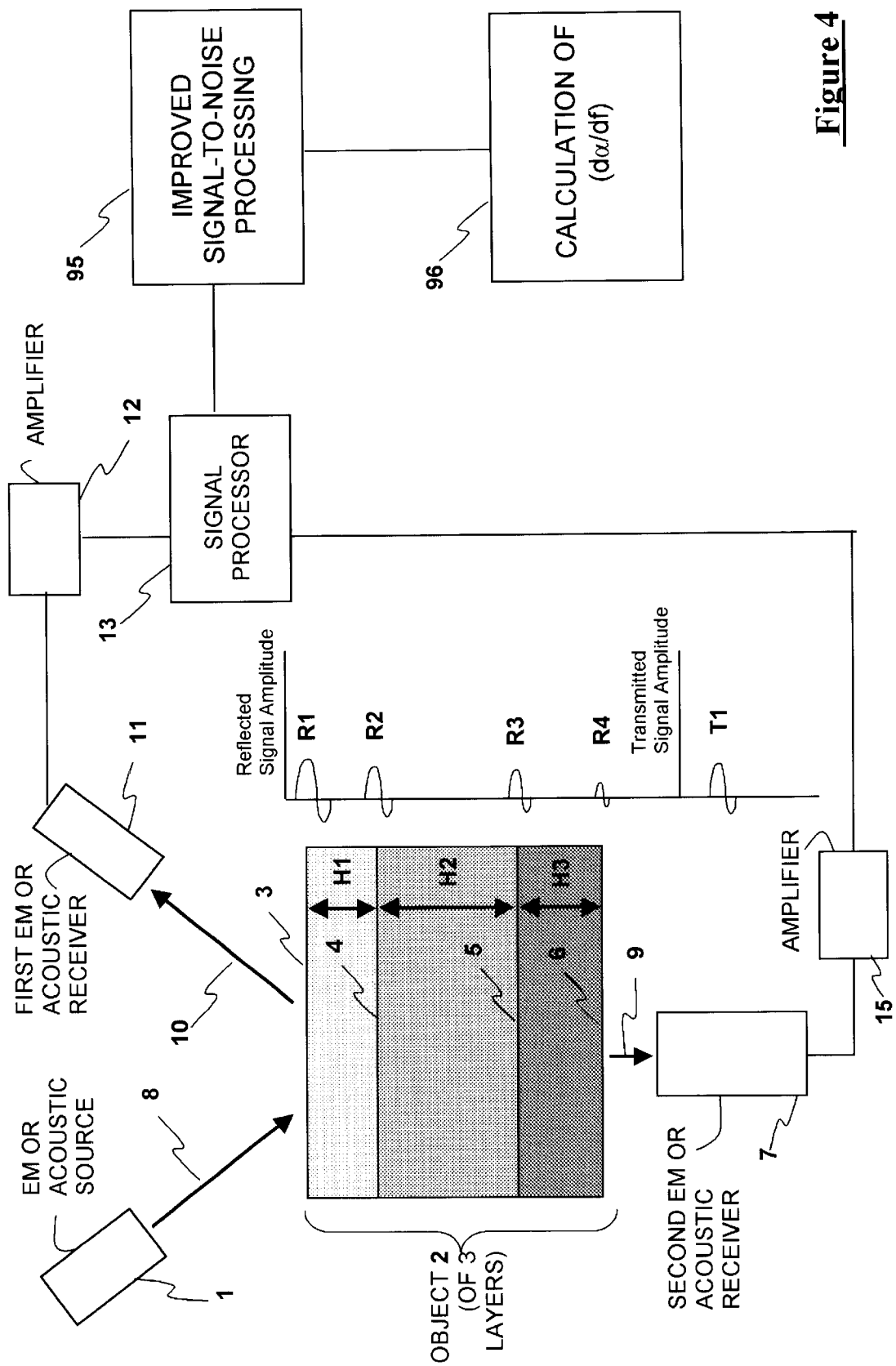
FIG. 4 Schematic representation of the improved apparatus of the present invention, as used for the analysis of an object comprising 3 layers.

An improved system, which can calculate the energy absorbed by a substance as a function of frequency, is illustrated schematically in FIG. 4. The system comprises a source of electromagnetic or acoustic energy 1, which transmits energy 8 towards an object 2. In this example, the object 2 comprises three distinct layers. As the energy 8 meets the object 2, it intercepts interface 3 between the air and the first layer of the object. A portion of the energy will be reflected from interface 3 as reflected energy, which is detected as a first signal of amplitude R1 by a first receiver 11. A portion of the energy 8 will be transmitted through the first layer of the object 2 (of thickness H1) and meet the interface 4 between the first and second layers of the object 2. At interface 4, a portion of the energy is reflected and detected as a second signal of amplitude R2 by the first receiver 11. A portion of the energy that meets interface 4 is further transmitted through the second layer of the object 2 (of thickness H2), to meet interface 5 between the second and third layers of the object 2. Again, at interface 5 a portion of the remaining transmitted energy is reflected from interface 5, and is detected as a third signal of amplitude R3 by the first receiver 11. The remaining transmitted energy that is not reflected at interface 5 is transmitted through the third layer of object 2 (of thickness H3) until it meets the interface 6 between the third layer of the object 2, and the air (i.e. the side of object 2 opposite the side to which energy is directed). At interface 6, a portion of the energy is reflected and detected as a fourth signal of amplitude R4 by receiver 11, and a portion of the energy is transmitted out of the object and detected as a signal of amplitude T1 by a second receiver 7. The four electromagnetic or acoustic signals (of amplitudes R1, R2, R3 and R4) received by the first receiver 11 are converted into a electronic signals, which are amplified by amplifier 12, and processed by signal processor 13. Furthermore, the remaining transmitted energy received by the second receiver 7 is converted to an electronic signal of amplitude T1, which is amplified by amplifier 15 and processed by signal processor 13. Importantly, the amplifiers 12 and 15 must ensure that the signal output is a linear function of gain. If non-linear gain devices are used, such as a log-amplifier, then the non-linearity must be known with a precision greater than the desired precision of the absorption calculations.

The thickness of each layer (H1, H2, and H3) may be calculated via separate measures. Techniques for measuring layer thickness are well known in the art and include the use of multiple sources and/or receivers to allow analysis of signals along multiple propagation paths. Velocity data may be readily determined for each path, and the thickness of each layer calculated. In addition, for some classes of materials, impedance/velocity data exists, and estimates of velocity (and thickness) can be made from impedance measurements.

The absorption characteristics of each layer of the object 2 (in db/m) may be calculated according to the following equations:

$$\text{Absorption}^{LAYER1} = (R1-R2)/H1 \quad (3)$$

$$\text{Absorption}^{LAYER2} = (R2-R3)/H2 \quad (4)$$

$$\text{Absorption}^{LAYER3} = (R3-R4)/H3 \quad (5)$$

By applying a number of pulses of electromagnetic or acoustic energy to the object, each of varying frequency, an analysis of the rate of change of absorption with respect to frequency can be carried out for each layer of object 2. Most materials exhibit a linear relationship between absorption and frequency over a specific range of frequencies. It is therefore possible to calculate a value for ($d\alpha/df$) for this frequency range, thus providing a ($d\alpha/df$) signature value that can be assigned to the substance. Following improved signal-to-noise processing 95, signal processor 13 can integrate the information gathered from the first and second receivers over the specified range of frequencies, and compute a value for ($d\alpha/df$) 96 for each of the three layers of object 2. Subsequent comparison of a database of known signature values can identify a match or close match for the substance. If, on occasion, further information is required to obtain a substance match, the signal processor 13 can further calculate the velocity and impedance characteristics of each layer, thus permitting the inclusion of addition parameters into the substance signature to assist object identification.

Figure 5:
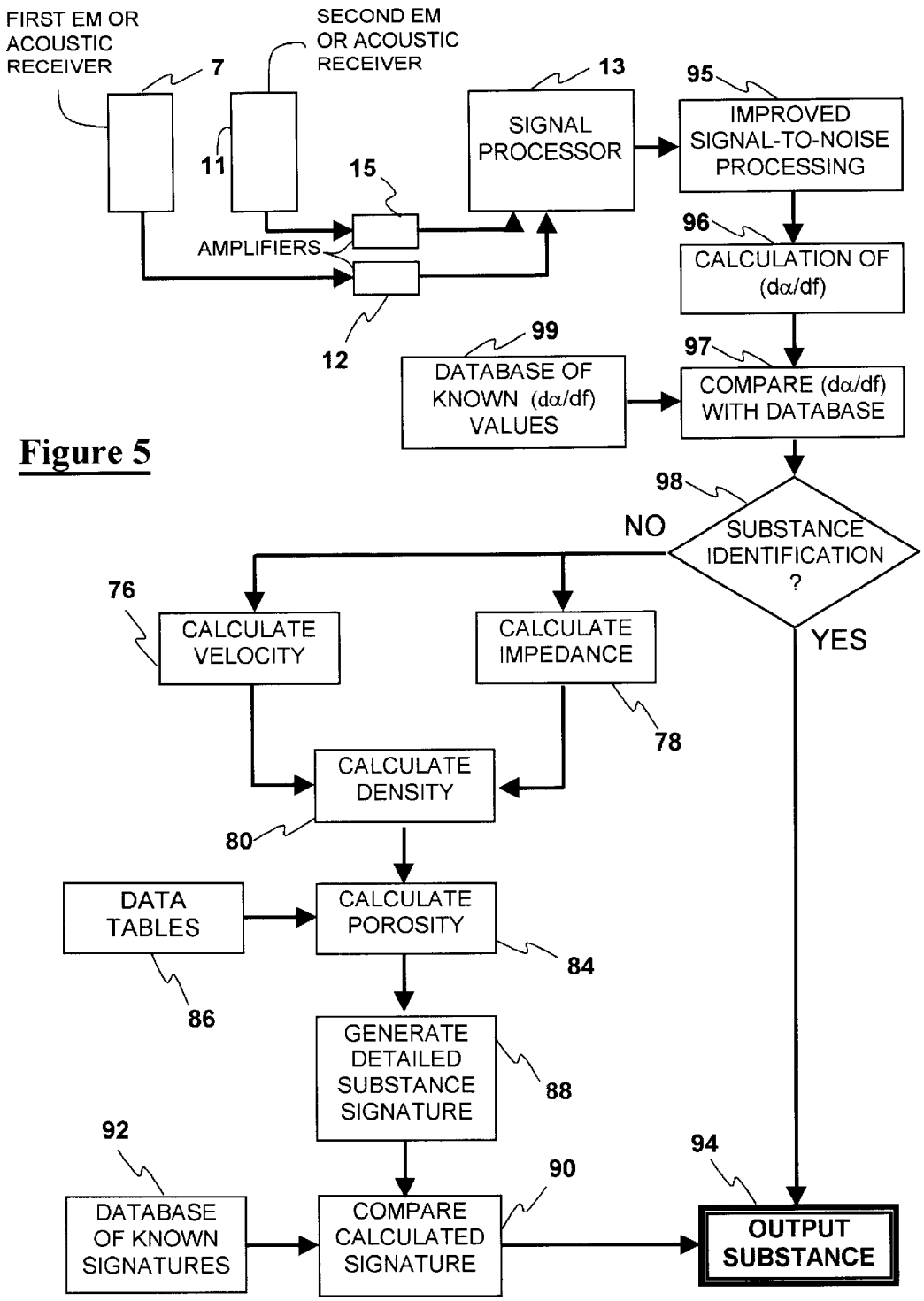
FIG. 5 Schematic representation of the processing steps carried out by the signal processor of the improved apparatus of the present invention.

The processing of the signal processor 13 of the improved apparatus is shown schematically in FIG. 5. Information received from the receivers 7 and 11 is relayed via amplifiers 12 and 15 respectively to the signal processor 13. Digital filters may be used for improved signal-to-noise processing of the received information at step 95.

The signal processor computes the ($d\alpha/df$) values at step 96 for each of the three layers. The signal processor then compares the ($d\alpha/df$) values via a first comparator at step 97 with those in a database of known ($d\alpha/df$) values 99 for known substances. If a match, or a sufficiently close match, is found at step 98 then the identification of the substance is outputted at step 94. However, if a match, or a sufficiently close match, is not found, then the signal processor continues on a default pathway similar to that described for the signal processor of U.S. Pat. No. 4,922,467. In this regard, the signal processor further calculates the velocity at step 76 and impedance at step 78, for each layer, as well as the density at step 80, and the porosity at step 84, for each substance. The porosity values can be further compared with data tables at step 86. By integration of the computed information, the signal processor generates and stores a detailed substance signature at step 88, and compares this signature with those of known stored signatures via a second comparator 90. The second comparator uses information in a database of known signatures 92 to identify the each substance. It is important to note that since the ($d\alpha/df$) value has already been calculated, this value remains a key component in the signature of each substance, facilitating the formulation of a complex and detailed signature. Once matches are found, the identification of the substances that comprise each layer can be outputted at step 94.

EXAMPLE 2

An example application for the improved apparatus of the present invention is shown schematically in FIGS. 6a, b, c and d. In this example, the apparatus of the present invention is used to analyze sediment layers beneath the ocean floor. For simplicity, only the reflected energy will be considered. The sediment layers are shown in FIG. 6a. Electromagnetic or acoustic energy is transmitted into the layers, and the reflected energy is detected by an arrangement of detectors similar to that in FIG. 1b. The first interface between the water and the silty sand reflects some of the transmitted energy, which is detected by a receiver positioned above the ocean floor (see FIG. 1b). The energy that is not reflected or refracted is transmitted through and partially absorbed by the silty sand until it meets the second interface between the silty sand and the sand. The silty sand will absorb some of this transmitted energy. Once the transmitted energy meets the second interface between the silty sand and the sand, a portion of the remaining energy is again reflected, as detected by a receiver positioned above the ocean floor. However, some of the remaining energy continues to be transmitted through and partially absorbed by the sand layer until it intercepts the sand/course sand interface. Again, a portion of the remaining energy is reflected by the interface and the some of the remaining energy is transmitted deeper into the ocean floor. In summary, energy transmitted into the ocean floor is reflected (and also refracted) at each material interface, and a portion continues to be transmitted through each layer of sediment, and a portion of this transmitted energy is absorbed by the material of the layer. Calculation of energy absorption of each layer, over a range of frequencies, can enable identification of the material comprising each layer.

For a specific frequency, the amplitude of the energy reflected at each of the three interfaces is represented schematically in FIG. 6b (arbitrary units). Moreover, analysis of the amplitude of received energy, specific for each interface over a range of frequencies, is shown schematically in FIG. 6c (arbitrary units). These graphs show typical curves expected for substances over a spectrum of frequencies. Generally, the amplitudes of the received signals are lower for interfaces that are further from the source of the transmitted signal. This is expected due to energy reflection and refraction at the preceding interfaces, as well as energy loss due to absorption at preceding layers.

For a particular frequency, the amount of energy absorbed by a layer may be calculated by considering the difference in amplitude of the reflected/refracted energy for the interface immediately preceding, and the interface immediately following the layer. Similar calculations may be carried out for a range of frequencies, thus resulting in an absorption graph for each layer. For the sake of simplicity examples have been chosen wherein the absorption for the material over a specific frequency range is a linear relationship of $(d\alpha/df)$. It is important to note that the technique is not limited to materials that exhibit a linear function. Some materials can exhibit complex functions that still permit the generation of a (complex) object signature with respect to $(d\alpha/df)$.

An example of a typical linear-type absorption graph is shown schematically for the silty sand layer in FIG. 6d. The absorption for materials is a linear function of frequency over specific ranges. Therefore, the slope of the linear portion of the graph can be calculated, thus providing the rate of change of absorption with respect to frequency $(d\alpha/df)$ over the linear range. Each substance is expected to have a specific value for $(d\alpha/df)$, permitting accurate identification and differentiation of substances. In this regard, specific classes of substance have been identified using this technique, without the requirement for additional calculations related to the velocity and impedance values of the material.

Figure 6:
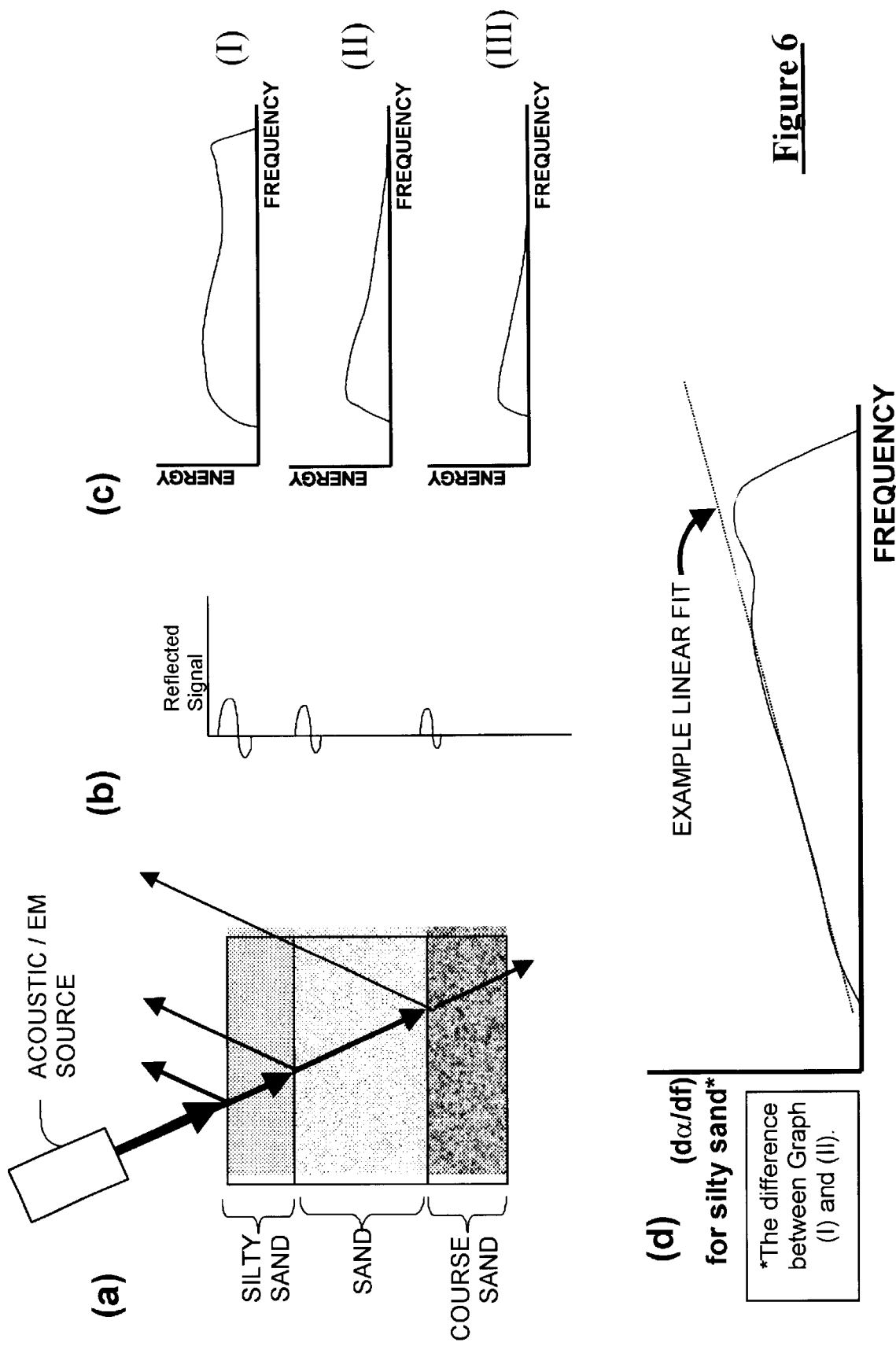
FIG. 6 Schematic representation of the analysis of absorption as function of frequency, for sediment layers beneath the ocean floor.

Although the example shown in FIG. 6 relates to marine sediments, the technique may also be applied for biological layers, metal layers, pollution layers, or objects buried within. In addition, the technique may be used to analyze geological anomalies caused by minerals, gas, glacial structures, oil etc. Moreover, specific software has been developed that is highly appropriate for analysis of transmitted, reflected and refracted signals, and subsequent calculations. An example of this type of software is Digital Spectral Analysis Version 50.00© (DSA50©), which enables graphical representation of sediment layers beneath the ocean floor.

The identification of some objects may involve energy source and/or receiver characteristics that are unknown, or which cannot be deduced. Under these circumstances, it is possible to resort to linear and non-linear absorption verses frequency databases, which assist in the classification of the unknown substance. For example, Table 1 shows theoretical absorption verses frequency data for clean non-contaminated and gas-free marine sediments. Similar databases have been developed for chemicals, explosives, and other objects. It is important to note that where frequency databases are available, a match may be found for a substance that exhibits a non-linear absorption verses frequency distribution.

TABLE 1

Typical Material Type Densities Vs. Absorption (db/m) (Theoretical model)

| Sediment (density) | FREQUENCY (KHz) | | | | | | | | | | |
| --- | --- | --- | --- | --- | --- | --- | --- | --- | --- | --- | --- |
| | 0.5 | 1 | 2 | 3 | 4 | 5 | 6 | 7 | 8 | 9 | 10 |
| Clay (1.1) | 0.06 | 0.11 | 0.22 | 0.30 | 0.44 | 0.55 | 0.66 | 0.77 | 0.88 | 0.90 | 1.10 |
| Clay (1.2) | 0.06 | 0.12 | 0.24 | 0.30 | 0.49 | 0.61 | 0.73 | 0.85 | 0.97 | 1.00 | 1.21 |
| Clayey silt (1.3) | 0.07 | 0.13 | 0.26 | 0.40 | 0.53 | 0.66 | 0.79 | 0.93 | 1.06 | 1.10 | 1.32 |
| Silty clay (1.4) | 0.07 | 0.14 | 0.29 | 0.40 | 0.57 | 0.72 | 0.86 | 1.00 | 1.15 | 1.20 | 1.43 |
| Sandysilt (1.5) | 0.08 | 0.17 | 0.33 | 0.50 | 0.66 | 0.83 | 0.99 | 1.16 | 1.32 | 1.40 | 1.65 |
| Silty sand (1.6) | 0.09 | 0.19 | 0.37 | 0.50 | 0.75 | 0.94 | 1.12 | 1.31 | 1.50 | 1.60 | 1.87 |
| Fine sand (1.7) | 0.10 | 0.21 | 0.42 | 0.60 | 0.84 | 1.05 | 1.26 | 1.47 | 1.68 | 1.80 | 2.09 |
| Course sand (1.8) | 0.12 | 0.23 | 0.46 | 0.60 | 0.93 | 1.16 | 1.39 | 1.62 | 1.85 | 2.00 | 2.31 |

EXAMPLE 3

A further example is described with regard to the analysis of electromagnetic energy absorption with respect to frequency. In this example, an electromagnetic energy transmitter was lowered into a river and pulses of electromagnetic energy were directed at the river bed. The pulses of electromagnetic energy were of known frequencies ranging from 166 MHz to 1000 MHz. The electromagnetic energy reflected from the river bed was analyzed for 6 difference energy frequencies. The average absorption of the top layer of the river bed was calculated for each frequency. Two different river bed sample materials were analyzed, namely clean sand and contaminated, unconsolidated clay. The results for the average absorptions for each of the sample materials is shown in Table 2.

TABLE 2

Comparison of absorption characteristics of river bed layers using EM energy.

| | FREQUENCY (MHz) | | | | | |
|---|---|---|---|---|---|---|
| Material | 166 | 333 | 500 | 666 | 833 | 1000 |
| CLEAN SAND | 25.55 | 25.355 | 25.4 | 29.7075 | 19.8775 | 24.29 |
| CONTAMINATED UNCONSOLIDATED CLAY | 33.865 | 35.28 | 39.0775 | 46.2525 | 42.6675 | 43.8075 |

Figure 7:
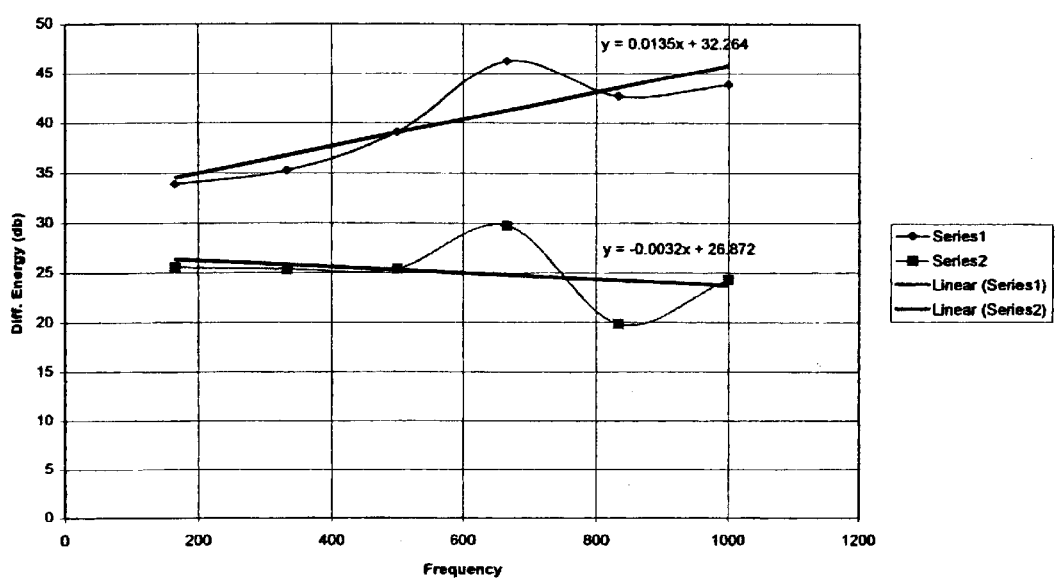
FIG. 7 Comparison of absorption characteristics of river bed layers, where Series 1 represents contaminated, unconsolidated clay, and Series 2 represents clean sand. Best fit linear relationships are also indicated.

The results detailed in Table 2 are shown graphically in FIG. 7. For both the clean sand (Series 2), and the contaminated, unconsolidated clay (Series 1), a best-fit line has been superimposed onto the graphs to provide a simple substance signature. The best fit lines provide an approximate linear relationship of absorption versus frequency for each material. Importantly, the clean sand exhibits a slightly negative linear relationship of absorption verses frequency, as indicated by the equation (y=−0.0032x+26.872). In direct contrast, the contaminated unconsolidated clay exhibits a positive linear relationship, as indicated by the equation (y=0.0135x+32.264). Therefore, river beds that are known to consist essentially of clean sand or contaminated, unconsolidated clay (or mixtures thereof) may be mapped according to their distribution of constituents using the simple linear ($d\alpha/df$) substance signatures provided by the best fit lines (FIG. 7).

Most river beds comprise a wide and varied range of substances. In this case it may be necessary to provide each substance with a more accurate and complex signature, rather than rely upon best-fit linear approximations of ($d\alpha/df$). For example, in the case of clean sand, a complex substance signature could be generated on the basis of the shape of the graph representing absorption as a function of frequency. Provision of similar complex signatures for other substances can permit differentiation of a wide range of river bed materials.

What is claimed is:

1. An apparatus for detecting the substance of an object contained within an enclosure, said apparatus comprising:
    electromagnetic or acoustic energy transmitter means for transmitting at least two pulses of electromagnetic or acoustic energy at a first side of said enclosure, said at least two pulses having differing frequencies;
    first electromagnetic or acoustic energy receiver means for receiving electromagnetic or acoustic energy that has been reflected from the object to produce at least two reflected electromagnetic or acoustic energy signals;
    second electromagnetic or acoustic energy receiver means for receiving electromagnetic or acoustic energy that has been transmitted or refracted through said object to produce at least two transmitted or refracted electromagnetic or acoustic energy signals;
    signal processor means connected to said transmitter means and to said first and second receiver means for producing an object signature, wherein said object signature is generated by computing energy absorption for each frequency and calculating a rate of change of said energy absorption as a function of frequency; and
    comparator means for comparing said object signature with signatures of known objects to determine the substance of said object.

2. The apparatus of claim 1, further including display means for providing an indication of the substance of the object.

3. The apparatus of claim 2, wherein said enclosure is a box and wherein said first electromagnetic or acoustic energy receiver means is located on said first side and said second electromagnetic or acoustic energy receiver means is located on a side of the box opposite said first side.

4. The apparatus of claim 2, wherein said enclosure is the earth and said first and second electromagnetic or acoustic energy receiver means are located on said first side, said second electromagnetic or acoustic energy receiver means being spaced further from said electromagnetic or acoustic energy transmitter means than said first electromagnetic or acoustic energy receiver means.

5. The apparatus of claim 3 or 4, wherein said signal processor means further processes said reflected electromagnetic or acoustic energy signals, and said transmitted or refracted electromagnetic or acoustic energy signals, to calculate an electromagnetic or acoustic impedance, an electromagnetic or acoustic velocity and a porosity of said object, wherein said object signature is further derived from the electromagnetic or acoustic impedance, the electromagnetic or acoustic velocity and the porosity of said object.

6. An apparatus according to claim 5, comprising at least one further electromagnetic or acoustic energy receiver means, for producing at least two further electromagnetic or acoustic energy signals, wherein each of said at least one further electromagnetic or acoustic energy receiver means is positioned to receive energy at a different angle relative to the energy transmitted at the object from the electromagnetic or acoustic energy transmitter means, said object signature being further derived from processing said at least two further electromagnetic or acoustic energy signals by said signal processor.

7. An apparatus for detecting the substance of an object within an enclosure, said apparatus comprising:
    electromagnetic or acoustic energy transmitter means for transmitting at least two pulses of electromagnetic or acoustic energy at a first side of said enclosure, said at least two pulses having different frequencies;
    movable electromagnetic or acoustic energy receiver means, movable about said object to receive reflected, transmitted or refracted energy in at least two positions relative to the energy transmitted at said object from the electromagnetic or acoustic energy transmitter means, said movable electromagnetic or acoustic energy receiver means producing at least two electromagnetic or acoustic energy signals at each of said at least two positions;
    signal processor means connected to said transmitter means and to said movable receiver means for producing an object signature, wherein said object signature is generated by computing energy absorption for each frequency and calculating a rate of change of absorption as a function of frequency; and
    comparator means for comparing said object signature with signatures of known objects to determine the substance of said object.

8. An apparatus for detecting the substance of an object contained within an enclosure, said apparatus comprising:
    electromagnetic energy transmitter means for transmitting a pulse of electromagnetic energy at a first side of said enclosure;
    first electromagnetic energy receiver means for receiving electromagnetic energy that has been reflected from the object to produce a reflected electromagnetic energy signal;

second electromagnetic energy receiver means for receiving electromagnetic energy that has been transmitted or refracted through said object to produce a transmitted or refracted electromagnetic energy signal;

signal processor means connected to said transmitter means and to said first and second receiver means, said signal processor means processing said transmitted pulse of electromagnetic energy, said reflected electromagnetic energy signal, and said refracted or transmitted electromagnetic energy signal to produce an object signature indicative of said object; and comparator means for comparing said object signature with signatures of known objects to determine the substance of said object.

9. The apparatus of claim 8, further including display means for providing an indication of the substance of the object.

10. The apparatus of claim 8, wherein said enclosure is a box and wherein said first electromagnetic energy receiver means is located on said first side and said second electromagnetic energy receiver means is located on a side of the box opposite to said first side.

11. The apparatus of claim 9, wherein said enclosure is the earth and said first and second electromagnetic energy receiver means are located on said first side, said second electromagnetic energy receiver means being spaced further from said electromagnetic energy transmitter means than said first electromagnetic energy receiver means.

12. The apparatus of claim 10 or 11, wherein said signal processor means processes said reflected electromagnetic energy signal and said transmitted or refracted electromagnetic energy signal, to calculate an electromagnetic impedance, an electromagnetic absorption, an electromagnetic velocity and a porosity of said object, wherein said object signature of said object is derived from the electromagnetic impedance, the electromagnetic absorption, the electromagnetic velocity and the porosity of said object.

13. An apparatus according to claim 12, comprising at least one further electromagnetic energy receiver means, for producing at least one further electromagnetic energy signal, wherein each of said at least one further electromagnetic energy receiver means is positioned to receive energy at a different angle relative to the energy transmitted at the object from the electromagnetic energy transmitter means, said object signature being further derived from processing said at least one further electromagnetic energy signal by said signal processor.

14. An apparatus for detecting the substance of an object within an enclosure, said apparatus comprising:

electromagnetic energy transmitter means for transmitting a pulse of electromagnetic energy at a first side of said enclosure;

movable electromagnetic energy receiver means movable about said object to receive reflected, transmitted or refracted energy in at least two positions relative to the pulse transmitted at said object from the electromagnetic energy transmitter means, said movable electromagnetic energy receiver means producing an electromagnetic energy signal in at least said at least two positions;

signal processor means connected to said transmitter means and to said movable receiver means said signal processor means processing said transmitted pulse of electromagnetic energy, and said reflected or refracted electromagnetic energy signals to produce an object signature indicative of said object; and comparator means for comparing said object signature with signatures of known objects to determine the substance of said object.

15. A method of determining the substance of an object located within an enclosure, the method comprising the steps of:

applying at least two pulses of electromagnetic or acoustic energy each of known intensities and differing frequencies to a first side of the enclosure and the object in the enclosure;

detecting at least two pulses of reflected electromagnetic or acoustic energy reflected from a surface of the object to provide reflected electromagnetic or acoustic energy signals;

detecting at least two pulses of transmitted or refracted electromagnetic or acoustic energy transmitted or refracted through the object to provide transmitted or refracted electromagnetic or acoustic energy signals;

processing said reflected and transmitted or refracted electromagnetic or acoustic energy signals to produce an object signature, said object signature comprising the electromagnetic or acoustic energy absorption of the substance as a function of frequency; and comparing the object signature so obtained with signatures of known objects to determine the substance of said object.

16. The method of claim 15, wherein the step of processing further includes the step of calculating an electromagnetic or acoustic impedance, an electromagnetic or acoustic velocity, and a porosity of the object, wherein the object signature is further derived from the electromagnetic or acoustic impedance, the electromagnetic or acoustic velocity and the porosity of the object.

17. The method of claim 15, wherein the enclosure is a box and the reflected electromagnetic or acoustic energy is detected on said first side of the enclosure and the transmitted or refracted electromagnetic or acoustic energy is detected on a side of the enclosure opposite said first side.

18. The method of claim 16, wherein the enclosure is a box and the reflected electromagnetic or acoustic energy is detected on said first side of the enclosure and the transmitted or refracted electromagnetic or acoustic energy is detected on a side of the enclosure opposite said first side.

19. The method of claim 15, wherein the enclosure is the earth and the reflected electromagnetic or acoustic energy and the transmitted or refracted electromagnetic or acoustic energy is detected on said first side of the enclosure and the transmitted or refracted electromagnetic or acoustic energy is detected at a position further away from the object than the reflected electromagnetic or acoustic energy is detected.

20. The method of claim 16, wherein the enclosure is the earth and the reflected electromagnetic or acoustic energy and the transmitted or refracted electromagnetic or acoustic energy is detected on said first side of the enclosure and the transmitted or refracted electromagnetic or acoustic energy is detected at a position further away from the object than the reflected electromagnetic or acoustic energy is detected.

21. A method of determining the substance of an object located within an enclosure, the method comprising the steps of:

applying electromagnetic energy to a first side of the enclosure and the object in the enclosure;

detecting the reflected electromagnetic energy reflected from a surface of the object to provide a reflected electromagnetic energy signal;

detecting the transmitted or refracted electromagnetic energy transmitted or refracted through the object to provide a transmitted or refracted electromagnetic energy signal;

processing said reflected and transmitted or refracted electromagnetic energy signals to produce an object signature; and comparing the object signature so obtained with signatures of known objects to determine the substance of said object.

22. The method of claim 21, wherein the step of processing further includes the step of calculating the electromagnetic impedance, the electromagnetic absorption, the electromagnetic velocity, and the porosity of the object, the object signature being further derived from the electromagnetic impedance, the electromagnetic absorption, the electromagnetic velocity and the porosity of said object.

23. The method of claim 21, wherein the enclosure is a box and the reflected electromagnetic energy is detected on said first side of the enclosure and the transmitted or refracted electromagnetic energy is detected on a side of the enclosure opposite said first side.

24. The method of claim 22, wherein the enclosure is a box and the reflected electromagnetic energy is detected on said first side of the enclosure and the transmitted or refracted electromagnetic energy is detected on a side of the enclosure opposite said first side.

25. The method of claim 21, wherein the enclosure is the earth and the reflected electromagnetic energy and the transmitted or refracted electromagnetic energy are detected on said first side of the enclosure and the transmitted or refracted electromagnetic energy is detected at a position further away from the object than the reflected electromagnetic energy is detected.

26. The method of claim 22, wherein the enclosure is the earth and the reflected electromagnetic energy and the transmitted or refracted electromagnetic energy are detected on said first side of the enclosure and the transmitted or refracted electromagnetic energy is detected at a position further away from the object than the reflected electromagnetic energy is detected.

* * * * *